(12) United States Patent
Sugarman et al.

(10) Patent No.: US 9,678,065 B2
(45) Date of Patent: Jun. 13, 2017

(54) LOW-COST POINT-OF-CARE ASSAY DEVICE

(71) Applicant: Becton, Dickinson and Company, Franklin Lakes, NJ (US)

(72) Inventors: Jeffrey Sugarman, Los Altos, CA (US); Wei Huang, Cupertino, CA (US); Justin Morton, Mentone (AU)

(73) Assignee: Becton, Dickinson and Company, Franklin Lakes, NJ (US)

( * ) Notice: Subject to any disclaimer, the term of this patent is extended or adjusted under 35 U.S.C. 154(b) by 797 days.

(21) Appl. No.: 14/152,954

(22) Filed: Jan. 10, 2014

(65) Prior Publication Data

US 2014/0200154 A1    Jul. 17, 2014

Related U.S. Application Data

(60) Provisional application No. 61/751,679, filed on Jan. 11, 2013.

(51) Int. Cl.
*B01L 3/00* (2006.01)
*G01N 33/53* (2006.01)
*G01N 33/569* (2006.01)

(52) U.S. Cl.
CPC .... *G01N 33/5302* (2013.01); *B01L 3/502723* (2013.01); *G01N 33/56972* (2013.01); *G01N 33/56988* (2013.01); *B01L 3/502715* (2013.01); *B01L 2200/0684* (2013.01); *B01L 2200/0689* (2013.01); *B01L 2200/141* (2013.01);
(Continued)

(58) Field of Classification Search
CPC ......... B01L 2200/141; B01L 2300/042; B01L 2300/048; B01L 2300/0663; B01L 2300/0825; B01L 2400/0406; B01L 3/502723; G01N 33/5302; G01N 33/56972; G01N 33/56988
See application file for complete search history.

(56) References Cited

U.S. PATENT DOCUMENTS 3,819,913 A    6/1974    Carter et al.
3,916,205 A   10/1975    Kleinerman
(Continued)

FOREIGN PATENT DOCUMENTS

EP    0737855 A1    10/1996
EP    0788615 B1     8/1997
(Continued)

OTHER PUBLICATIONS

Bornheimer et al., "Development of the BD FACSPresto™ System for Point-of-Care Determination of CD4 absolute count %CD4, and total Hb", BD Biosciences IAS FACSPresto Poster (2013), 1 page.
(Continued)

*Primary Examiner* — Jennifer Wecker
(74) *Attorney, Agent, or Firm* — Bret E. Field; Bozicevic, Field & Francis LLP

(57) ABSTRACT

The present disclosure provides methods and systems for analyzing a liquid sample. A micro-fluidic device to perform an assay of a liquid sample is described that includes a sample application site and a vent outlet in fluid communication with the capillary channel. A cap is provided that is configured to seal both the vent outlet and the sample application site in a shared volume and separate from an outside environment.

22 Claims, 2 Drawing Sheets

(52) U.S. Cl.
CPC ... *B01L 2300/042* (2013.01); *B01L 2300/048* (2013.01); *B01L 2300/0663* (2013.01); *B01L 2300/0825* (2013.01); *B01L 2400/0406* (2013.01)

(56) References Cited

U.S. PATENT DOCUMENTS

| | | | |
|---|---|---|---|
| 3,963,350 A | 6/1976 | Watanabe et al. | |
| 4,088,448 A | 5/1978 | Lilja et al. | |
| 4,125,828 A | 11/1978 | Resnick et al. | |
| 4,133,873 A | 1/1979 | Noller | |
| 4,337,222 A | 6/1982 | Kitajima et al. | |
| 4,501,496 A | 2/1985 | Griffin | |
| 4,727,020 A | 2/1988 | Recktenwald | |
| 4,751,188 A | 6/1988 | Valet | |
| 4,857,735 A | 8/1989 | Noller | |
| 4,959,305 A | 9/1990 | Woodrum | |
| 5,053,626 A | 10/1991 | Tillotson | |
| 5,073,857 A | 12/1991 | Peters et al. | |
| 5,102,625 A | 4/1992 | Milo | |
| 5,134,662 A | 7/1992 | Bacus et al. | |
| 5,159,642 A | 10/1992 | Kosaka | |
| 5,187,749 A | 2/1993 | Sugimoto | |
| 5,196,709 A | 3/1993 | Berndt | |
| 5,200,152 A | 4/1993 | Brown | |
| 5,294,799 A | 3/1994 | Aslund et al. | |
| 5,332,905 A | 7/1994 | Brooker et al. | |
| 5,348,859 A | 9/1994 | Brunhouse et al. | |
| 5,385,539 A | 1/1995 | Maynard | |
| 5,489,771 A | 2/1996 | Beach et al. | |
| 5,491,343 A | 2/1996 | Brooker | |
| 5,528,045 A | 6/1996 | Hoffman et al. | |
| 5,547,849 A | 8/1996 | Baer et al. | |
| 5,554,536 A * | 9/1996 | Rising | B01L 3/50255 422/561 |
| 5,556,764 A | 9/1996 | Sizto et al. | |
| 5,592,291 A | 1/1997 | Iida | |
| 5,599,668 A | 2/1997 | Stimpson et al. | |
| 5,627,037 A | 5/1997 | Ward et al. | |
| 5,661,558 A | 8/1997 | Nogami et al. | |
| 5,674,457 A | 10/1997 | Williamsson et al. | |
| 5,675,155 A | 10/1997 | Pentoney et al. | |
| 5,681,529 A | 10/1997 | Taguchi et al. | |
| 5,692,503 A | 12/1997 | Kuenstner | |
| 5,732,150 A | 3/1998 | Zhou et al. | |
| 5,733,721 A | 3/1998 | Hemstreet et al. | |
| 5,773,301 A | 6/1998 | Ziegler | |
| 5,851,835 A | 12/1998 | Groner | |
| 5,898,487 A | 4/1999 | Hage | |
| 6,043,880 A | 3/2000 | Andrews et al. | |
| 6,064,474 A | 5/2000 | Lee et al. | |
| 6,064,897 A | 5/2000 | Lindberg et al. | |
| 6,094,592 A | 7/2000 | Yorkey et al. | |
| 6,103,197 A | 8/2000 | Werner | |
| 6,154,282 A | 11/2000 | Lilge et al. | |
| 6,159,740 A | 12/2000 | Hudson et al. | |
| 6,181,418 B1 | 1/2001 | Palumbo et al. | |
| 6,187,592 B1 | 2/2001 | Gourley | |
| 6,214,629 B1 | 4/2001 | Freitag et al. | |
| 6,226,347 B1 | 5/2001 | Golenhofen | |
| 6,262,798 B1 | 7/2001 | Shepherd et al. | |
| 6,294,094 B1 | 9/2001 | Muller et al. | |
| 6,305,804 B1 | 10/2001 | Rice et al. | |
| 6,342,376 B1 | 1/2002 | Kozian et al. | |
| 6,345,191 B1 | 2/2002 | Hartmann et al. | |
| 6,350,613 B1 | 2/2002 | Wardlaw et al. | |
| 6,410,341 B1 | 6/2002 | Freitag et al. | |
| 6,453,060 B1 | 9/2002 | Riley et al. | |
| 6,477,394 B2 | 11/2002 | Rice et al. | |
| 6,479,299 B1 | 11/2002 | Parce et al. | |
| 6,493,567 B1 | 12/2002 | Krivitski et al. | |
| 6,519,025 B2 | 2/2003 | Shepherd et al. | |
| 6,563,585 B1 | 5/2003 | Rao et al. | |
| 6,594,075 B1 | 7/2003 | Kanao | |
| 6,611,320 B1 | 8/2003 | Lindberg et al. | |
| 6,612,111 B1 | 9/2003 | Hodges | |
| 6,638,769 B2 | 10/2003 | Lilja et al. | |
| 6,665,060 B1 | 12/2003 | Zahniser et al. | |
| 6,696,240 B1 | 2/2004 | Kloepfer et al. | |
| 6,716,588 B2 | 4/2004 | Sammak et al. | |
| 6,723,290 B1 | 4/2004 | Wardlaw | |
| 6,740,527 B1 | 5/2004 | Wong et al. | |
| 6,825,921 B1 | 11/2004 | Modlin et al. | |
| 6,828,567 B2 | 12/2004 | Amirkhanian et al. | |
| 6,831,733 B2 | 12/2004 | Pettersson et al. | |
| 6,858,400 B2 | 2/2005 | Bristow | |
| 6,862,534 B2 | 3/2005 | Sterling et al. | |
| 6,869,570 B2 | 3/2005 | Wardlaw | |
| 6,898,458 B2 | 5/2005 | Zeng et al. | |
| 6,960,165 B2 | 11/2005 | Ueno et al. | |
| 6,985,224 B2 | 1/2006 | Hart | |
| 6,999,173 B2 | 2/2006 | Kleinfeld et al. | |
| 7,075,628 B2 | 7/2006 | Shepherd et al. | |
| 7,094,562 B2 | 8/2006 | Bittner | |
| 7,096,124 B2 | 8/2006 | Sterling et al. | |
| 7,115,841 B2 | 10/2006 | Zeng et al. | |
| 7,133,545 B2 | 11/2006 | Douglass et al. | |
| 7,146,372 B2 | 12/2006 | Bacus et al. | |
| 7,149,332 B2 | 12/2006 | Bacus et al. | |
| 7,271,912 B2 | 9/2007 | Sterling et al. | |
| 7,279,134 B2 | 10/2007 | Chan et al. | |
| 7,303,922 B2 | 12/2007 | Jeng et al. | |
| 7,319,894 B2 | 1/2008 | Higgins | |
| 7,324,674 B2 | 1/2008 | Ozawa et al. | |
| 7,420,660 B2 | 9/2008 | Muller | |
| 7,426,407 B2 | 9/2008 | Higgins | |
| 7,477,382 B2 | 1/2009 | Grey et al. | |
| 7,515,268 B1 | 4/2009 | Ayliffe et al. | |
| 7,518,727 B2 | 4/2009 | Pentoney et al. | |
| 7,539,335 B2 | 5/2009 | Fukuyama | |
| 7,560,073 B1 | 7/2009 | Peter et al. | |
| 7,625,712 B2 | 12/2009 | Paul et al. | |
| 7,630,063 B2 | 12/2009 | Padmanabhan et al. | |
| 7,674,598 B2 | 3/2010 | Paul et al. | |
| 7,738,094 B2 | 6/2010 | Goldberg | |
| 7,762,946 B2 | 7/2010 | Sugimoto | |
| 7,781,226 B2 | 8/2010 | Mcdevitt et al. | |
| 7,790,464 B2 | 9/2010 | Tarasev | |
| 7,816,135 B2 | 10/2010 | Goldberg | |
| 7,826,728 B2 | 11/2010 | Konno et al. | |
| 7,854,891 B2 | 12/2010 | Yamamoto et al. | |
| 7,892,551 B2 | 2/2011 | Glencross | |
| 7,903,241 B2 | 3/2011 | Wardlaw et al. | |
| 7,952,692 B2 | 5/2011 | Primack et al. | |
| 8,009,894 B2 | 8/2011 | Lindberg et al. | |
| 8,125,623 B2 | 2/2012 | Munger et al. | |
| 8,224,058 B2 | 7/2012 | Lindberg et al. | |
| 8,244,021 B2 | 8/2012 | Lett et al. | |
| 8,306,594 B2 | 11/2012 | Paseman et al. | |
| 8,353,848 B2 | 1/2013 | Long et al. | |
| 8,377,398 B2 | 2/2013 | McDevitt et al. | |
| 8,406,859 B2 | 3/2013 | Zuzak et al. | |
| 8,483,789 B2 | 7/2013 | Higgins | |
| 8,488,903 B2 | 7/2013 | Higuchi | |
| 8,541,227 B2 | 9/2013 | Christensen et al. | |
| 2003/0152927 A1 * | 8/2003 | Jakobsen | B01L 3/5027 435/6.16 |
| 2003/0170613 A1 | 9/2003 | Straus | |
| 2003/0175947 A1 * | 9/2003 | Liu | B01F 11/0071 435/288.5 |
| 2003/0230728 A1 | 12/2003 | Dai et al. | |
| 2004/0189311 A1 * | 9/2004 | Glezer | B01L 3/5027 324/444 |
| 2004/0224329 A1 | 11/2004 | Gjerde et al. | |
| 2005/0142565 A1 | 6/2005 | Samper et al. | |
| 2005/0190058 A1 | 9/2005 | Call | |
| 2006/0024756 A1 | 2/2006 | Tibbe et al. | |
| 2006/0183236 A1 | 8/2006 | Berlin et al. | |
| 2006/0227325 A1 | 10/2006 | Rulison et al. | |
| 2006/0241495 A1 | 10/2006 | Kurtz | |
| 2006/0252079 A1 | 11/2006 | Oldham et al. | |
| 2007/0132994 A1 | 6/2007 | Kobayashi et al. | |
| 2007/0178009 A1 | 8/2007 | Sakaino et al. | |
| 2008/0190220 A1 | 8/2008 | Backes et al. | |

(56) References Cited

U.S. PATENT DOCUMENTS

| | | | |
|---|---|---|---|
| 2008/0203319 | A1 | 8/2008 | Pentoney et al. |
| 2008/0268469 | A1 | 10/2008 | Srienc et al. |
| 2009/0075324 | A1 | 3/2009 | Pettersson |
| 2009/0181411 | A1 | 7/2009 | Battrell et al. |
| 2009/0317806 | A1 | 12/2009 | Hasson |
| 2010/0291599 | A1 | 11/2010 | Tague, Jr. et al. |
| 2011/0118139 | A1 | 5/2011 | Mehta et al. |
| 2013/0041236 | A1* | 2/2013 | Pugia ................ A61B 10/0045 600/309 |
| 2013/0045529 | A1 | 2/2013 | Goldberg et al. |
| 2013/0162990 | A1 | 6/2013 | Kobayashi et al. |
| 2015/0125882 | A1 | 5/2015 | Bornheimer et al. |
| 2015/0132789 | A1 | 5/2015 | Bornheimer et al. |

FOREIGN PATENT DOCUMENTS

| | | |
|---|---|---|
| EP | 0821784 B1 | 11/1998 |
| EP | 0959346 A2 | 11/1999 |
| EP | 0663070 B1 | 5/2000 |
| EP | 0681177 B1 | 7/2000 |
| EP | 0744600 B1 | 8/2001 |
| EP | 0818682 B1 | 10/2001 |
| EP | 0809807 B1 | 7/2002 |
| EP | 0800074 B1 | 7/2003 |
| EP | 0969279 B1 | 10/2003 |
| EP | 1347702 A2 | 10/2003 |
| EP | 1456649 B1 | 7/2006 |
| EP | 1701150 A1 | 9/2006 |
| EP | 1324021 B1 | 1/2008 |
| EP | 1924195 A2 | 5/2008 |
| EP | 1990638 A1 | 11/2008 |
| EP | 2041549 | 4/2009 |
| EP | 2083687 A1 | 8/2009 |
| EP | 1405073 B1 | 3/2010 |
| EP | 2232442 A1 | 9/2010 |
| EP | 1698883 B1 | 1/2011 |
| EP | 2016390 B1 | 4/2013 |
| EP | 2605020 A2 | 6/2013 |
| EP | 1558934 B1 | 7/2013 |
| JP | 2000292354 A | 10/2000 |
| JP | 2002-506208 A | 2/2002 |
| JP | 2002-516982 | 6/2002 |
| JP | 2006515065 A | 5/2006 |
| JP | 2001088098 | 7/2008 |
| JP | 2008525768 | 7/2008 |
| WO | WO 99/20998 A1 | 4/1999 |
| WO | WO 99/45384 A1 | 9/1999 |
| WO | 00/29847 A2 | 5/2000 |
| WO | WO 00/28297 A2 | 5/2000 |
| WO | WO 02/44729 A1 | 6/2002 |
| WO | WO 02/50518 A2 | 6/2002 |
| WO | WO 03/036290 A1 | 5/2003 |
| WO | 2004017374 A2 | 2/2004 |
| WO | 2004/100887 A2 | 11/2004 |
| WO | 2005100539 A2 | 10/2005 |
| WO | WO2006047831 | 5/2006 |
| WO | WO 2006/096126 A1 | 9/2006 |
| WO | WO 2006/116616 A2 | 11/2006 |
| WO | WO 2006/119368 A2 | 11/2006 |
| WO | WO2007012975 A1 | 2/2007 |
| WO | 2007/033318 A2 | 3/2007 |
| WO | WO 2007/051861 A1 | 5/2007 |
| WO | WO 2007/111555 A1 | 10/2007 |
| WO | WO 2008/002462 A2 | 1/2008 |
| WO | WO 2008/010761 A1 | 1/2008 |
| WO | 2008/037068 A1 | 4/2008 |
| WO | WO 2008/103992 A2 | 8/2008 |
| WO | WO 2009/091318 A1 | 7/2009 |
| WO | WO 2010/085658 A1 | 7/2010 |
| WO | WO 2011/133540 A2 | 10/2011 |
| WO | WO 2013/075031 A1 | 5/2013 |

OTHER PUBLICATIONS

Beach, J. M. "A LED light calibration source for dual-wavelength microscopy," Cell Calcium, 21 (1 ): 63-68 (1997).

Cheng et al. "A microfluidic device for practical label-free CD4+ T cell counting of HIV-infected subjects," Lab Chip, 7: 170-178 (2007).

Debernardi et al. "Single cell Ca2+/cAMP cross-talk monitoring by simutaneous Ca2+/cAMP fluorescence ratio imaging," Proc. Natl. Acad. Sci. 93:4577-4582 (1996).

Fischer et al. "An affordable, portable fluorescent imaging device for skin lesion detection using a dual wavelength approach for image contrast enhancement and aminolaevulinic acid-induced protoporphyrin IX. Part I. Design, spectral and spatial characteristics," Lasers Med Sci., 16: 199-296 (2001).

Fischer et al. "An affordable, portable fluorescent imaging device for skin lesion detection using a dual wavelength approach for image contrast enhancement and aminolaevulinic acid-induced protoporphyrin IX. Part II. In vivo testing," Lasers Med Sci., 16: 207-212 (2001).

Gerstner et al. "Quantitative Histology by Multicolor Slide-based Cytometry," Cytometry Part A, 50A: 210-219 (2004).

Hart et al. "Light emitting diode excitation emission matrix fluorescence spectroscopy," Anlayst. (127): 1693-1699 (2002).

Heiden et al. "New Epi-Fluorescence optical system for independent analysis of two different fluorochromes in microscopy," Cytometry 20: 95-101 (1995).

Holland et al. "Point-of-care molecular diagnostic systems -past, present and future," Current Opinion in Microbiology, 8: 504-509 (2005).

Janossy et al. " Precise CD4 T-Cell counting using red diode laser excitation: for richer, for poorer," Cytometry (Clinical Cytometry) 50: 78-85 (2002).

Kassotis et al. "An inexpensive dual-excitation apparatus for fluorescence microscopy," Pfugers Arch., 409:47-51 (1987).

Lewis et al. "Color-blind fluorescence detection for four-color DNA sequencing"; PNAS; www.pnas.org/cgi/ doi/10/1073/pnas. 0501606102; Apr. 12, 2005; vol. 102, No. 5: 5346-5351.

Li et al. "CD4 T lymphocytes enumeration by an easy-to-use single platform Image cytometer for HIV monitoring in resource-constrained settings," Cytometry Part B (Clinical Cytometry) 728: 397-407 (2007).

Myers et al. "Innovations in optical microfluidic technologies for point-of-care diagnostics", Lab on a Chip, vol. 8, pp. 2015-2031 (2008).

Rodriguez et al. "A microchip CD4 counting method for HIV monitoring in resource-poor settings," PLoS Medicine, 2 (7): 0663-0672 (2005).

Shapiro, "Cellular astronomy—a foreseeable future in cytometry," Cytometry Part A, 60A: 115-124 (2004).

Shapiro, "Personal cytometers: Slow flow or no flow,"Cytometry Part A, 69A: 620-630 (2006).

Fukano et al. "Fast dual-excitation radiometry with light-emitting diodes and high-speed liquid crystal shutters," Biochemical and Biophysical Research Communications, 340:250-255 (2006).

Toner et al. "Blood-on-a-chip," Annu. Rev. Biomed. Eng. 7: 77-103 (2005).

Tsien et al. "Measurement of cytosolic free Ca2+ in individual small cells using fluorescence microscopy with dual excitation wavelengths," Cell Calcium 6:145-157 (1985).

Warner et al. "Multicomponent analysis in clinical chemistry by use of rapid scanning fluorescence spectroscopy," Clin. Chern. 22/9: 1483-1492 (1967).

Wittrup et al. "Fluorescence array detector for large-field quantitative fluorescence cytometry," Cytometry 16: 206-213 (1994).

Yager et al. "Microfluidic diagnostic technologies for global public health," Nature 442: 412-418 (2006).

Ymeti et al. "A single platform image cytometer for resource-poor settings to monitor disease progression in HIV infection," Cytometry Part A 71A: 132-142 (2007).

Malmstadt et al. "'Smart' mobile affinity matrix for microfluidic immunoassays," Lab on a Chip 2004, vol. 4, pp. 412-415.

(56) References Cited

OTHER PUBLICATIONS

Tsougeni et al. "'Smart' polymeric microfluidics fabricated by plasma processing: controlled wetting, capillary filling and hydrophobic valving," Lab on a Chip 2010, vol. 10, pp. 462-469.
Fridley et al., Controlled release of dry reagents in porous media for tunable temporal and spatial distribution upon rehydration, Lab Chip. Nov. 7, 2012;12(21):4321-4327.

* cited by examiner

LOW-COST POINT-OF-CARE ASSAY DEVICE

CROSS-REFERENCE TO RELATED APPLICATIONS

Pursuant to 35 U.S.C. §119 (e), this application claims priority to the filing date of the U.S. Provisional Patent Application Ser. No. 61/751,679, filed Jan. 11, 2013, the disclosure of which is incorporated herein by reference.

INTRODUCTION

Point-of-care diagnosis refers to the process of obtaining a biological sample from a subject, testing the sample for the presence of one or more analytes of interest to obtain a result and then providing a diagnosis to the subject based on the sample analysis results, all at the same location. Point-of care diagnosis offers significant benefits in terms of cost savings and patient satisfaction, since diagnoses can often be made more quickly and for less cost than more traditional diagnostic testing procedures, e.g., where a sample is obtained at a first location and then shipped for testing to a second location.

Most of the current point-of-care tests for infectious diseases offer only a single diagnosis per test. Rapid diagnosis of multiple infectious diseases from a single fingerstick blood drop using an inexpensive and facile technology available at the point-of-care location would greatly improve global health outcomes. Flow cytometry-based micro-particle immunoassays provide excellent accuracy and multiplexing, but are inappropriate for point-of-care settings due to cumbersome sample preparation and expensive instrumentation.

SUMMARY

A micro-fluidic device to perform an assay of a liquid sample is described that includes a sample application site and a vent outlet in communication with a capillary channel. A cap is configured to seal the vent outlet and the sample application site inside a shared volume and separate both the sample application site and vent outlet from an outside environment. In some embodiments the device may include a capillary channel and a venting channel. In some embodiments the device may include a liquid barrier surrounding the application site, wherein the liquid barrier is disposed between the application site and the vent outlet, preventing applied sample from blocking the vent outlet. In some embodiments the liquid barrier may include a raised edge surrounding the application site. In some embodiments the liquid barrier includes a depression surrounding the application site. In some embodiments the capping element includes a gasket.

Aspects of the invention further include a micro-fluidic device configured to perform an assay of a liquid sample, where the device includes a connected sample application site, capillary channel, hydrophobic junction, venting channel, and a vent outlet. A capping element is configured to seal the vent outlet and the sample application site from an outside environment. The capping element encloses a shared volume around the sample application site and the vent outlet. In some embodiments the hydrophobic junction includes a hexane treated area of the capillary channel.

Aspects of the invention further include a method for performing an assay of a liquid sample. Aspects of the methods include applying a liquid sample to a sample application site in fluid communication with a capillary channel; wherein the liquid sample flows via a capillary action force through the capillary channel. Venting for the air displaced by the liquid sample is provided through a venting channel and vent outlet. The method includes, in some instances, sealing the liquid sample from the outside environment with a capping element, wherein the capping element provides for a sealed volume of air shared by the sample application site and the vent outlet. In some embodiments the micro-fluidic device includes a capillary channel and a venting channel. In some embodiments the device includes a liquid barrier surrounding the sample application site wherein the liquid barrier separates the sample application site from the vent outlet. In some embodiments the liquid barrier includes a raised edge or a depression surrounding the application site. In some embodiments the capping element includes a gasket.

A method of producing an assay cartridge is described that includes forming a sample application site and a capillary channel in fluid communication with each other. The device may include a capillary channel and a venting channel. The channels may be formed by forming a grooved path in a plastic material (e.g., cycloolefin polymer) and treating the grooved path with plasma in order to increase the hydrophilicity of the treated area. A portion of the surface area of the grooved path may be contacted with a non-polar organic solvent (e.g., hexane, heptane, pentane, chloroform or any combination thereof) wherein the treatment reduces the hydrophilicity of the surface area. The grooved path may be sealed to form a capillary channel and a hydrophobic junction.

DETAILED DESCRIPTION

Figure 1:
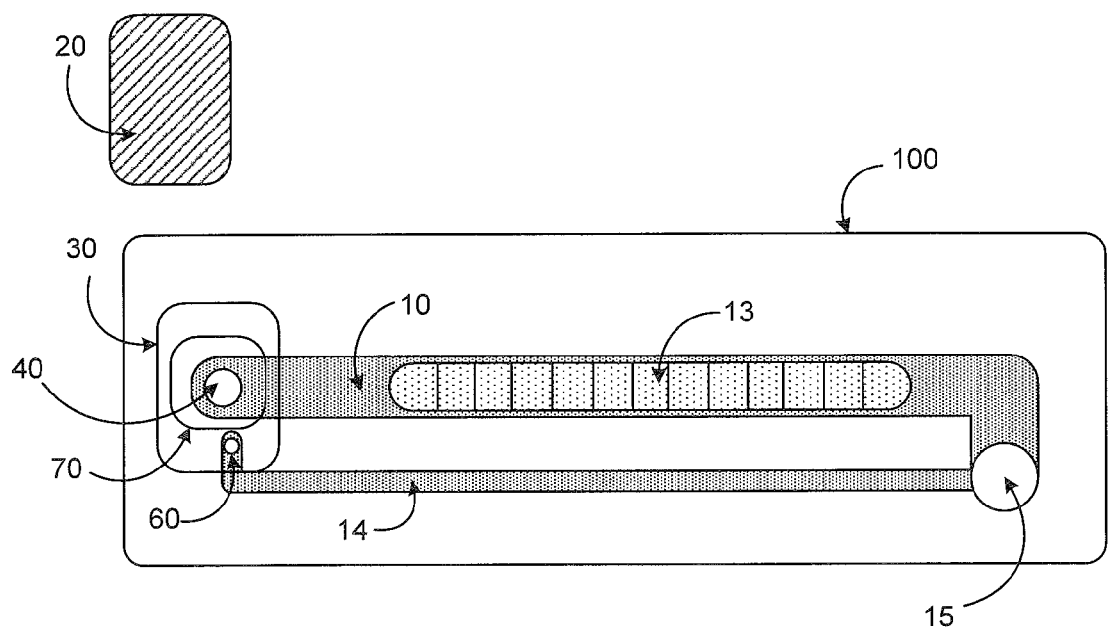
FIG. 1 provides a schematic illustration of an assay device of an embodiment of this invention.

The present disclosure provides methods and systems for analyzing a liquid sample. A micro-fluidic device to perform an assay of a liquid sample is described that includes a sample application site and a vent outlet in fluid communication with the capillary channel. A cap is provided that is configured to seal both the vent outlet and the sample application site in a shared volume and separate from an outside environment.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The practice of the present invention may employ, unless otherwise indicated, conventional techniques from molecular biology (including recombinant techniques), cell biology, immunoassay technology, microscopy, image analysis, and analytical chemistry, which are within the skill of the art. Such conventional techniques include, but are not limited to, detection of fluorescent signals, image analysis, selection of illumination sources and optical signal detection components, labeling of biological cells, and the like. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press); Murphy, Fundamentals of Light Microscopy and Electronic Imaging (Wiley-Liss, 2001); Shapiro, Practical Flow Cytometry, Fourth Edition (Wiley-Liss, 2003); Herman et al, Fluorescence Microscopy, 2nd Edition (Springer, 1998); all of which are herein incorporated in their entirety by reference for all purposes.

In further describing various aspects of the invention, embodiments of micro-fluidic devices of the invention are reviewed first in greater detail, followed by a review of various embodiments of the methods of making and using the devices, as well as embodiments of kits that include the devices.

Devices

A micro-fluidic device is described that includes a capillary channel in communication with both a sample application site and a vent outlet. By micro-fluidic device is meant a device that is configured to control and manipulate fluids geometrically constrained to a small scale (e.g., sub-millimeter). In addition to the sample application site, capillary channel and vent outlet, aspects of the devices include a cap that is configured to seal the vent outlet and the sample application site within the same volume and separate the two components from an outside environment.

As the devices include a capillary channel, they include an elongated structure that is configured to provide for capillary flow of liquid therethrough. The device may utilize any force such as gravity or centrifugal force in addition to capillary force to provide movement of the sample through the capillary channel. As the capillary channel has an elongated structure, it has a length that is longer than its width. While the ratio of length to width may vary, in some instances the ratio of length to width ranges from 2 to 5000, such as 5 to 500 and include 15 to 20. In some instances, the length of the channel ranges from 10 to 500, such as 20 to 250 and including 50 to 75 mm. In some instances, the channels have a micrometer sized longed cross-sectional dimension, e.g., a longest cross-sectional dimension (e.g., diameter in the case of the tubular channel) ranging from 0.1 to 20, such as 1 to 10 and including 3 to 5 mm. In some instances the width of the channel ranges from 0.1 to 20, such as 1 to 10 and including 3 to 5 mm. In some instances the height of the channel ranges from 5 to 500, such as 10 to 150 and including 20 to 70 microns. While the cross sectional shape of the capillary channels may vary, in some instances, cross-sectional shapes of channels of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc.

Positioned at one end of capillary channel (i.e., the proximal end) is a sample application site. The sample application site is a site or location configured to receive a volume of sample, e.g., a biological sample, to be analyzed. In some instances, the sample application site is a structure configured to receive a sample having a volume ranging from 5 to 100, such as 10 to 50 and including 20 to 30 microliters. The sample application site can have any convenient shape, so long as it provides for fluid access, either directly or through an intervening component(s) that provides for fluidic communication, to the capillary channel.

Also present in the micro-fluidic devices is a vent outlet. Vent outlets are configured to provide for fluidic communication, e.g., for gas, from the distal end of the capillary channel to the outer surface of the device. While the cross sectional shape of the vent outlet may vary, in some instances, cross-sectional shapes of vent outlets of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc. The length of the longest cross-sectional dimension (e.g., diameter in the case of a circular shaped vent) of the vent outlet may also vary, ranging in some instances from 0.2 to 2, such as 0.5 to 1.5 and including 0.8 to 1.2. The outlet vent is positioned on the device in a location that is proximal or near the sample application site. While the shortest distance between the sample application site and outlet vent may vary, in some instances the shortest distance between these two components of the device ranges from 1 to 20, such as 5 to 15 and including 8 to 10 mm_.

As summarized above, in addition to the sample application site, capillary channel and vent outlet, aspects of the devices include a cap that is configured to seal the vent outlet and the sample application site within the same volume and separate the two components from an outside environment. The cap is a component that is covered to cover both the sample application and outlet vent in a sealing manner, e.g., as described in greater detail below. While the dimensions of the cap may vary, in some instances, the cap is dimensioned to cover a surface area that ranges from 10 to 1000, such as 50 to 500 and including 100 to 300 mm$^2$. In some instances, the cap is moveably attached to another location of the device, e.g., as described in greater detail below.

In some aspects the cap seals over the sample application site that is connected to a capillary channel in the device in order to contain bio-hazardous sample within the device and/or to prevent evaporation. The capillary channel that fills from the application site with sample liquid may be connected through a venting channel to a vent outlet that ends inside the same volume that may be covered by the cap. The same cap may prevent bio-hazardous material from coming out the vent outlet or the sample application site and at the same time ensuring that there is equalization of pressure on both the front and back of the liquid column in the capillary channel. In some embodiments the cap may be closed as soon as liquid is applied to the device, with no impact on the rate at which the device will fill. If a liquid barrier (e.g., hydrophobic junction) within the device fails, the liquid is still contained within the device because no part of the application site or vent outlet is open to the outside environment after the cap has been closed.

In addition to the capillary channel, sample application site, vent outlet and cap (e.g., as described above) the device for performing the assay may include any number of features for performing a desired assay, which features include, but are not limited to, a mixing (i.e., sample/reagent combination) chamber, a reaction channel, an analyte specific capture domain, a hydrophobic junction, a venting channel, etc., or any combination thereof.

In some instances, positioned in the fluidic path between the sample application site and the capillary channel is a mixing chamber. By mixing chamber is meant an area or location in the fluidic path that is configured to combine sample which has been applied to the sample application and is flowing to the capillary channel with one or more reagents. The mixing chamber may or may not include active mixing components, e.g., stir bars, etc. In some instances, the mixing chamber includes a structure that provides for high surface area upon which one or more reagents may be positioned, where the high surface area structure may or may not be configured to filter one or more components of the sample flowing therethrough. In some instances, the high surface area structure may be one that is configured to not filter can components of the sample flowing therethrough. For example, where the sample is a whole blood sample, the high surface area structure may be one that is configured not to impede the flow of any of the whole blood components, e.g., white blood cells, red blood cells, platelets, etc., through the high surface area structure. In such instances, the high surface area structure may have a porosity ranging from 20 to 80, such as 30 to 70 and including 40 to 60. The high surface area structure, when present, may be fabricated from any suitable material, e.g., polymeric materials, glass materials, ceramic materials, metallic materials, etc. Specific materials of interest include, but are not limited to: polyethylene, polypropylene, polyvinylidine fluoride, and the like.

Present in the mixing chamber is one or more reagents, which reagents may be present on a surface of a high surface area structure when present. A variety of different reagents may be present in the mixing chamber or domain of the device, depending on the particular assay for which the device is configured. Reagents of interest include labeled specific binding members, enzymes, substrates, oxidizers, etc., among others.

In some embodiments, the reagent(s) of the mixing chamber include a labeled specific binding member. A labeled specific binding member may include a specific binding domain and a label domain. The terms "specific binding," "specifically binds," and the like, refer to the preferential binding of a domain (e.g., one binding pair member to the other binding pair member of the same binding pair) relative to other molecules or moieties in a solution or reaction mixture. The specific binding domain may bind (e.g., covalently or non-covalently) to a specific epitope of an analyte of interest. In certain aspects, specific binding domain non-covalently binds to a target. In such instances, the specific binding domain association with the binding target (e.g., cell surface marker) may be characterized by a KD (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less.

A variety of different types of specific binding domains may be employed as the capture ligands. Specific binding domains of interest include, but are not limited to, antibody binding agents, proteins, peptides, haptens, nucleic acids, etc. The term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'2 fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

The label domain may be detectable based on, for example, fluorescence emission maxima, fluorescence polarization, fluorescence lifetime, light scatter, mass, molecular mass, or combinations thereof. In certain aspects, the label domain may be a fluorophore (i.e., a fluorescent label, fluorescent dye, etc.). Fluorophores can be selected from any of the many dyes suitable for use in analytical applications (e.g., flow cytometry, imaging, etc.). A large number of dyes are commercially available from a variety of sources, such as, for example, Molecular Probes (Eugene, Oreg.) and Exciton (Dayton, Ohio). Examples of fluorophores that may be incorporated into the microparticles include, but are not limited to, 4-acetamido-4'-isothiocyanatostilbene-2,2' disulfonic acid; acridine and derivatives such as acridine, acridine orange, acridine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide;

anthranilamide; Brilliant Yellow; coumarin and derivatives such as coumarin, 7-amino-4-methylcoumarin (AMC, Coumarin 120), 7-amino-4-trifluoromethylcoulurarin (Coumaran 151); cyanine and derivatives such as cyanosine, Cy3, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; or combinations thereof. Other fluorophores or combinations thereof known to those skilled in the art may also be used, for example those available from Molecular Probes (Eugene, Oreg.) and Exciton (Dayton, Ohio). The fluorescent label may be distinguishable based on fluorescence emission maxima, and optionally further based on light scatter or extinction.

The amount of reagent(s) present in the mixing chamber or domain may vary, e.g., depending on the particular type of assay for which the device is configured. In some instances, the amount of a reagent is sufficient to provide for a concentration of reagent in the sample following flow through the mixing chamber that ranges from 0.002 to 100, such as 0.02 to 10 and including 0.2 to 1 microgram/mL. While the dry weight of a reagent present in the mixing chamber may vary, in some instances the dry weight ranges from 0.01 to 500, such as 0.3 to 120 and including 3 to 12 ng.

In some embodiments the micro-fluidic device includes a capillary channel separated from a venting channel by a hydrophobic junction. When present, the venting channel may have a variety of different configurations and is configured to couple the vent outlet with the end of the capillary channel furthest from the sample application site in fluidic communication. The venting channel may be an elongated structure, such that it has a length that is longer than its width. While the ratio of length to width may vary, in some instances the ratio of length to width ranges from 5 to 2000 such as 10 to 200 and include 50 to 60. In some instances, the length of the venting channel ranges from 5 to 200, such as 10 to 100 and including 50 to 75 mm. In some instances, the venting channels have a micrometer sized longed cross-sectional dimension, e.g., a longest cross-sectional dimension (e.g., diameter in the case of the tubular channel) ranging from 0.1 to 10, such as 0.5 to 5 and including 1 to 2 mm. In some instances the width of the venting channel ranges from 0.1 to 10, such as 0.5 to 5 and including 1 to 2 mm. In some instances the height of the channel ranges from 0.5 to 5, such as 0.2 to 2 and including 0.5 to 1 mm. While the cross sectional shape of the venting channels may vary, in some instances, cross-sectional shapes of the venting channels of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc.

As reviewed above, the capillary channel may be separated from the venting channel by a hydrophobic region. By hydrophobic region is meant a region or domain that is resistant to being wetted by water, e.g., it repels aqueous media. The hydrophobic region may be one that has a surface energy that is lower than the surface energy of the surfaces of the capillary channel. The magnitude of difference in surface energies may vary, ranging in some instances from 5 to 500, such as 10 to 30 dynes/cm_. The surface energy of the hydrophobic domain may also vary, ranging in some instances from 20 to 60, such as 30 to 45 dynes/cm, e.g., as measured using the protocol described in ASTM Std. D2578. The dimensions of the hydrophobic region are configured to at least partially if not complete impede liquid flow of sample past the hydrophobic region. While the dimensions of the region may vary, in some instances the hydrophobic region has a surface area ranging from 0.5 to 50, such as 2 to 20 and including 7 to 15 mm$^2$. The hydrophobic region may be provided using any convenient approach, e.g., by fabricating the device from a suitable hydrophobic material in the hydrophobic region, by treating a surface of the device with a hydrophobic material, etc., e.g., as described in greater detail below.

In some instances, the device may include an analyte specific capture domain. An analyte specific capture domain is a domain or region of the capillary channel from which a result may be read during use of the device. The analyte specific capture domain is positioned at some distance downstream from the sample application site of the device. By "downstream" is meant the direction that the sample flows by capillary action, i.e., the direction of fluid flow from the sample application site. The total distance fluid flows between the sample receiving region and the detection region may vary, ranging in some instances from 2 to 500 cm, such as 10 to 100 cm and including 20 to 50 cm.

The analyte specific capture domain is a region that includes an amount of a capture probe, also referred to herein as a "detection capture probe." A detection capture probe is immobilized in the analyte specific capture domain and specifically binds to target molecule of interest, e.g., an analyte, a control molecule, etc. The size of the detection capture probe region may vary, and in some instances the capture probe region can have an area ranging from 0.01 to 0.5 cm$^2$, such as 0.05 to 0.1 cm$^2$ and including 0.1 to 0.2 cm$^2$. An analyte specific capture domain can have a variety of different configurations, where the configuration can be random or the configuration can have a specific shape such as a line, circle, square, or more complex shape, such as a "+", as desired. A given analyte specific capture domain can include a single capture probe or two or more different capture probes, where each of the two or more different capture probes, where when the detection region includes two or more capture probes, the capture probes can be distinct from each other (i.e., bind to different target molecules), as desired.

In some embodiments an analyte specific capture domain may be provided that includes particles displaying a specific binding member(s) for a target molecule(s), e.g., an analyte(s) of interest, a control or reference molecule, etc. For example, in some embodiments the device may include an analyte specific capture domain comprised of capture beads immobilized on a convenient surface, e.g., the upper surface, of a domain of the capillary channel, e.g., a capillary chamber in the capillary channel, e.g., as described in PCT Application Serial No. PCT/US2012/065683 filed on Nov. 16, 2012 and hereby incorporated by reference. The capture beads may be coated with a binding reagent that specifically binds to the analyte of interest. In some embodiments, the capture beads are coated with an antigen to which the antibody of interest specifically binds. In such instances, a fluorescently labeled reagent for detection may be added that specifically binds to the analyte, enabling the detection of the captured analyte by its fluorescence emissions. The capture beads may be immobilized to a spot on the upper surface of the capillary chamber through any suitable means. In some instances, beads stayed localized in the spot by passive interactions between the beads and the capillary chamber surface, but covalent binding can be used, as desired.

Capture beads coated with different antigens can be localized in different spots within the capillary chamber to enable the multiplexed detection of multiple analytes. Alternatively, capture beads coated with different antigens can be distinguishably labeled using fluorescent dyes that are distinguishable from each other and from the dye-labeled detection reagents that are used to measure the captured analytes. In this manner, the beads can be immobilized in the same spot, but distinguished by their fluorescent emissions. In other embodiments, labeling reagents may be disposed at an analyte specific capture domain disposed at the sample application site and labeled sample may flow to a reaction chamber in the capillary channel for detection.

In some instances, the device may include a quality control domain in the capillary channel, e.g., positioned near the end of the channel furthest from the sample application site. The quality control channel may vary, and may for example include a capture member, e.g., antibody, specific for a labeled reagent, etc., such as described in greater detail below, e.g., to provide a confirmation that sample flows through the device during a given assay.

In some instances, the device may include one or more identifiers, which identifiers may provide information about the device, e.g., the particular assay for which it is configured, manufacturing lot number, etc., which identifiers may be unique identifiers. The identifiers may be human and/or machine readable, e.g., may be text or a bar code, as desired.

Aspects of the devices having now been generally described, certain embodiments of the devices are now reviewed in great detail in terms of the figures. Referring to FIG. 1, a device for performing an assay of a liquid sample is described. The device 100 may be comprised of a capillary channel 10 formed in any rigid or semi rigid material (e.g. glass, polymer, ceramic etc.). A cap 20 is illustrated separate from the device but may be attached by any mechanism such as a hinge or joint. The cap 20 may seal an area 30 from the environment in which a sample application site 40 is located.

In some instances, the device and or cap material is flexible so that a good seal may be formed between the cap 20 and the underlying material. Of course, it may be possible to use a rigid or semi-rigid material for the cap 20. For example, glass or plastic may be used to form the cap 20. A gasket or other sealing aid (not shown) may be optionally utilized.

The sample application site 40 is in fluid communication with capillary channel 10. The sample application site 40 may comprise dried reagents for labeling or reacting with the sample as it flows through the sample application site, which may or may not be associated with a high surface area structure, e.g., as described in greater detail above. A venting channel 14 may be connected to the capillary channel at any point along the capillary channel (e.g., end venting or side venting). In some embodiments the capillary channel 10 may be separated from the venting channel 14 by a hydrophobic junction region 15. The hydrophobic junction may be a predetermined area of reduced hydrophilicity relative to the hydrophilicity of the capillary channel, e.g., as described above.

The hydrophilicity of the capillary channel and the hydrophobic junction may be adjusted by any means. In some embodiments, the hydrophilicity of the capillary channel may be adjusted by means of plasma treatment of a first predetermined area of the micro-fluidic device. The predetermined area may be a groove or channel area in a plastic material such as a cyclo-olefin polymer. All or part of the material or channel area may be treated with a plasma field to increase the hydrophilicity of the treated area. A hydrophobic region may be prepared by any means used to decrease the hydrophilicity of a second predetermined area of the micro-fluidic device material relative to the channel area. The first and second predetermined areas may overlap.

In some instances, the hydrophobic region is produced via application of a suitable solvent. For example, the hydrophobic region may be formed by the application of any solvent that may cause temporary liquefication or swelling of the micro-fluidic device material. In some embodiments, the hydrophobic region is formed by the application of solution comprising a non-polar organic solvent, such as hexane, heptane, pentane and chloroform, or any combination of two or more of such solvents, to a second predetermined area of the plastic material (e.g., cyclo-olefin polymer) for a period of time sufficient to produce the desired hydrophobicity in the region. In some embodiments a polar solvent may be used to reduce the hydrophilicity of a second predetermined area of the microfluidic device. The second predetermined area may overlap with the first predetermined area. The solvent may subsequently evaporate from the area, leaving a region of reduced hydrophilicity. The capillary channel and hydrophobic junction may be created by applying a sealed cover to the groove or channel area. The hydrophobic junction may provide an impediment of liquid flow in the capillary channel between the capillary channel and the vent outlet or venting channel.

As reviewed above, in some embodiments the microfluidic device may comprise reagents for reaction with the sample. Those reagents may be located at predetermined areas of the device, such a mixing chamber (not shown) or the sample application site 40 or along the capillary channel 10. The capillary channel 10 may comprise an optically transmissive wall 13 or wall(s) (e.g., top and bottom) for the detection of (and/or irradiation of) analytes in a sample. The capillary channel may be connected to a venting channel 14 or vent outlet 60 located in the area 40 that is covered by the cap 30. The sample application site and vent outlet may be covered by the cap and therefore isolated from the environment in a shared space. The shared space may provide for an isolated volume shared with the vent outlet and sample application site. The two openings may be protected from liquid communication with each other by any means, such as a raised edge 70 or moat (not shown) separating the sample application site from the vent outlet. If a raised edge is provided, the height it may rise may vary, in some instances ranging from 0.2 to 5, such as 0.5 to 1.5 mm. If a moat or depression is provided, the depth of such structure may vary, in some instances ranging from 0.2 to 5, such as 0.5 to 1.5 mm.

The cap of this invention seals the application site and vent outlet from the outside environment inside a shared air space, while not negatively impacting the flow into the capillary channel. In some embodiments, the cap has sealing gaskets or other flexible parts that may cause the volume and pressure of the air inside the cap and venting channel to be changed. Changes in air pressure within the shared air space due to temperature changes during the incubating and detection of the device are applied equally to the front and back of the liquid column in the micro-fluidic device and therefore do not result in substantial fluid motion. Once saturated with water vapor from the sample, the volume of shared air space does not allow further evaporation derived either from the sample application site or vent outlet.

Micro-fluidic bio-diagnostic devices that fill through capillary action do so because the flow surfaces are hydrophilic, and wetting of the surfaces is energetically favorable. Such devices may be configured for the incoming sample to displace the gas, e.g., air, resident in the device. It is desirable for both the applied sample as well as the vented air to be contained within the cartridge in order to protect users from potentially bio-hazardous material. It is also desirable for the sample within the device to not appreciably evaporate, which may change the ratio of sample components. A cap may be used to seal the sample material within the device after the sample has been supplied. Since some devices may fill over a period of minutes, it is also desirable for the user to be able to secure the cap onto the device after sample has been applied but before the sample has completely filled into the capillary channel. If means are not provided otherwise to prevent it, liquid flow will be impeded by vacuum created in the capped application site as the liquid enters the capillary, but air is prevented from entering the application site by the cap. The solution is met by terminating the vent outlet of the micro-fluidic channel in an air space that is both sealed from the outside and is shared with the sample application area. In this way, regardless of whether the cap is placed before or after the liquid flow is complete, the air pressure is the same in front of and behind the liquid column in the capillary channel. The volume of air displaced through the vent outlet by the liquid filling the channel replaces the volume of liquid leaving the sample application site. Even if air inside the cap is slightly pressurized during compression of the cap gasket onto its sealing surface, the increase in pressure in front of and in back of the liquid column remains constant so the net driving force for flow into the capillary channel is not impacted. In addition, at any point during the incubation (minutes to hours) or reading of the device, if the temperature of the device changes, the pressure inside the cap may change, but such changes will not cause motion of the fluid in the channel since the pressure is the same in both the front and back of the liquid column.

In some embodiments of the present invention any combination of the following features may be utilized in the device. For example the capillary channel or the sample application site may include a mixing chamber where dried, e.g., preserved, reagents may be located. The dimensions of the capillary channel may impact the imaging and flow of sample in the channel. In some embodiments the channel may be between 2 and 10 mm wide, such as between 3 and 5 mm or between 3 and 4 mm wide. In some embodiments the capillary channel may be between 1 and 1000 microns deep, such as between 20 and 60 microns deep or between 40 and 60 microns deep. Depths less than 60 microns deep may beneficially provide for imaging white blood cells in a whole blood sample by minimizing the obscuring effects of red blood cells. The capillary channel may be any length that provides for capillary flow along a channel. In some embodiments the capillary channel may be between 10 and 100 mm long.

The device is suitable for assays to detect analytes, such as antibodies, in a sample comprising a biological fluid, such as urine, saliva, blood, e.g., whole blood. As reviewed above, in some embodiments the device may comprise an analyte specific capture domain comprised of capture beads immobilized on the upper surface of a capillary chamber in the capillary channel, e.g., as described in PCT Application Serial No. PCT/US2012/065683 filed on Nov. 16, 2012 and hereby incorporated by reference. The capture beads may be coated with a binding reagent that specifically binds to the analyte of interest. In some embodiments, the capture beads are coated with an antigen to which the antibody of interest specifically binds. A fluorescently labeled reagent for detection is added that specifically binds to the analyte, enabling the detection of the captured analyte by its fluorescence emissions. The capture beads may be immobilized to a spot on the upper surface of the capillary chamber through any suitable means. In some instances, beads stayed localized in the spot by passive interactions between the beads and the capillary chamber surface, but covalent binding can be used.

Capture beads coated with different antigens can be localized in different spots within the capillary chamber to enable the multiplexed detection of multiple analytes. Alternatively, capture beads coated with different antigens can be distinguishably labeled using fluorescent dyes that are distinguishable from each other and from the dye-labeled detection reagents that are used to measure the captured analytes. In this manner, the beads can be immobilized in the same spot, but distinguished by their fluorescent emissions. In other embodiments, labeling reagents may be disposed at an analyte specific capture domain disposed at the sample application site and labeled sample may flow to a reaction chamber in the capillary channel for detection.

The fluorescence of the captured analytes can be measured using an inexpensive digital imaging/image processing system. Suitable systems and method for imaging samples in capillary channels are described in U.S. Pat. No. 8,248,597 issued Aug. 21, 2012 and U.S. patent application Ser. No. 13/590,114 filed Aug. 20, 2012. Suitable imagers are described in U.S. Pat. Nos. 7,927,561, and 7,738,094, both incorporated herein by reference.

In some embodiments the micro-particles may be disposed on the top surface of the capillary channel. During the typical incubation time of for immunoassays (e.g. between 2 and 60 minutes such as between 10 and 30 minutes), red blood cells in whole blood will settle to the bottom, leaving clearer plasma at the top. By placing the micro-particles on the top surface of the channel, potential interference of the fluorescence detection from red blood cells is eliminated, allowing a simple assay for whole blood without separation.

In some embodiments, the present invention is used to detect serological concentrations of human antibodies in fingerstick volumes (5-50 μL) of whole blood in a no-wash format, e.g., as described below in the Experimental section.

Methods

Aspects of the methods include applying a sample to an application site and allowing the sample (e.g., a biological sample, such as blood or blood product comprising an analyte) to flow through a capillary channel, followed by detection of one or more target analytes in the sample.

As such, methods of the invention may include providing a sample-contacted sample application site of a test device of the invention. A "sample-contacted sample application site" is a sample application site that has been contacted by sample. In practicing methods of the invention, a sample-contacted sample application site is provided by applying a sample to the sample application site of the device. The amount of sample that is applied to the sample application site may vary, so long as it is sufficient to provide for the desired capillary flow and operability of the assay. The sample may be applied to the sample application site using any convenient protocol, e.g., via dropper, pipette, syringe and the like. In addition to providing a sample-contacted sample application site, the methods can further include applying a quantity of a suitable liquid, e.g., buffer, to provide for adequate fluid flow through the bibulous member. Any suitable liquid may be employed, including but not limited to buffers, cell culture media (e.g., DMEM), etc. Buffers include, but are not limited to: tris, tricine, MOPS, HEPES, PIPES, MES, PBS, TBS, and the like. Where desired, detergents may be present in the liquid, e.g., NP-40, TWEEN™ or TritonX100 detergents.

In some embodiments, the sample-contacted sample application site is provided by combining the sample with one or more assay components (e.g., a reagent, a buffer, and the like) prior to applying the sample which has the assay component(s) to the sample application site. When the sample is combined with one or more assay components prior to the application of the sample having the assay component(s) to the sample application site, the combination may be achieved using any convenient protocol. The amount of an assay component(s), when combined with the sample, may vary as desired. In some embodiments, the sample-contacted sample application site is provided by applying one or more assay components (e.g., as described above) to the sample receiving application site prior to applying the sample to the sample application site. In some embodiments, the sample-contacted sample application site is provided by applying the sample to the sample application site prior to applying one or more assay components (e.g., as described above) to the sample application site. As mentioned above, in some embodiments, the device includes one or more assay components (e.g., reagent, such as described above). In such cases, the sample-contacted sample application site is provided by applying the sample to the sample application site, e.g., without prior combination with one or more assay components.

Following sample application, the sample is allowed to flow through the capillary channel, and one or more portions of the channel, e.g., the detection region, including the entire channel, is then read or evaluated to determine whether the analyte(s) of interest is present in the sample. The channel or one or more portions thereof may be read after a predetermined period of time following sample application, where this period of time may range from 10 sec to 1 hour, such as 30 sec to 30 min, e.g., 30 sec to 10 min, including 30 sec to 1 min The capillary channel or one or more portions thereof may be read using a protocol that depends on the nature of the assay and analyte to be detected. For example, radiolabels can be detected using photographic film or scintillation counters, fluorescent markers can be detected using one or more illuminators, e.g., lasers, LEDs, and one or more photodetectors, e.g., PMTs, CCDs, to detect emitted light. Enzymatic labels are typically detected by providing the enzyme with a substrate and detecting the reaction product produced by the action of the enzyme on the substrate, metal labels can be detected by simply visualizing the colored label or can be detected using laboratory equipment capable of detecting metal, and colorimetric labels are detected by simply visualizing the colored label. Accordingly, in those instances where the label employed is a fluorescent label, the method may include irradiating the sample in the capillary channel or a portion thereof with light of a wavelength suitable to excite the label and then detecting light emitted from the fluorescent label, e.g., through the viewing window of a housing of the device. As such, a subsequent step in methods of the invention may include reading a detection region of the capillary channel of the device to determine whether the analyte is present in the sample.

As indicated above, methods of the invention may include a step of placing the sample loaded device into a suitable reader and obtaining an assay result from the reader. For example, the fluorescence of the captured analytes can be measured using an inexpensive digital imaging/image processing system. Suitable systems and method for imaging samples in capillary channels are described in U.S. Pat. No. 8,248,597 issued Aug. 21, 2012 and U.S. patent application Ser. No. 13/590,114 filed Aug. 20, 2012. Suitable imagers are described in U.S. Pat. Nos. 7,927,561, and 7,738,094, both incorporated herein by reference.

In some embodiments, the method is a method of determining whether an analyte is present in the sample in an amount that meets or exceeds a predetermined threshold. As such, when the amount of analyte of interest in the sample surpasses a particular threshold (also referred to as a "predetermined threshold"), the signal in the detection region (resulting from the binding of competitor to capture probe in the detection region) is detectable. The threshold or predetermined threshold may be determined by multiple differentially weighted factors (e.g., the number of capture probes in the sample receiving region that bind to the analyte, the binding affinity of the capture probe for the analyte, and the like).

Utility

The methods, devices, and kits of the invention find use in a variety of different applications and can be used to determine whether an analyte is present in a multitude of different sample types from a multitude of possible sources. Depending on the application and the desired output of the methods described herein, an analyte may be detected in a qualitative manner ("present" vs "absent"; "yes, above a predetermined threshold" vs "no, not above a predetermined threshold"; etc.) or a quantitative manner, e.g., as an amount in a sample (such as concentration in sample). Many different types of analytes can be analytes of interest, including but not limited to: proteins (including both free proteins and proteins bound to surface of a structure, such as a cell), nucleic acids, viral particles, and the like. Further, samples can be from in vitro or in vivo sources, and samples can be diagnostic samples.

In practicing methods of the invention, the samples can be obtained from in vitro sources (e.g., extract from a laboratory grown cell culture) or from in vivo sources (e.g., a mammalian subject, a human subject, a research animal, etc.). In some embodiments, the sample is obtained from an in vitro source. In vitro sources include, but are not limited to, prokaryotic (e.g., bacterial) cell cultures, eukaryotic (e.g., mammalian, fungal) cell cultures (e.g., cultures of established cell lines, cultures of known or purchased cell lines, cultures of immortalized cell lines, cultures of primary cells, cultures of laboratory yeast, etc.), tissue cultures, column chromatography eluants, cell lysates/extracts (e.g., protein-containing lysates/extracts, nucleic acid-containing lysates/extracts, etc.), viral packaging supernatants, and the like. In some embodiments, the sample is obtained from an in vivo source. In vivo sources include living multi-cellular organisms and can yield diagnostic samples.

In some embodiments, the analyte is a diagnostic analyte. A "diagnostic analyte" is an analyte from a sample that has been obtained from or derived from a living multi-cellular organism, e.g., mammal, in order to make a diagnosis. In other words, the sample has been obtained to determine the presence of one or more disease analytes in order to diagnose a disease or condition. Accordingly, the methods are diagnostic methods. As the methods are "diagnostic methods," they are methods that diagnose (i.e., determine the presence or absence of) a disease (e.g., sickness, diabetes, etc.) or condition (e.g., pregnancy) in a living organism, such as a mammal (e.g., a human). As such, certain embodiments of the present disclosure are methods that are employed to determine whether a living subject has a given disease or condition (e.g., diabetes). "Diagnostic methods" also include methods that determine the severity or state of a given disease or condition.

In certain embodiments, the methods are methods of determining whether an analyte is present in a diagnostic sample. As such, the methods are methods of evaluating a sample in which the analyte of interest may or may not be present. In some cases, it is unknown whether the analyte is present in the sample prior to performing the assay. In other instances, prior to performing the assay, it is unknown whether the analyte is present in the sample in an amount that is greater than (exceeds) a predetermined threshold amount. In such cases, the methods are methods of evaluating a sample in which the analyte of interest may or may not be present in an amount that is greater than (exceeds) a predetermined threshold.

Diagnostic samples include those obtained from in vivo sources (e.g., a mammalian subject, a human subject, and the like.) and can include samples obtained from tissues or cells of a subject (e.g., biopsies, tissue samples, whole blood, fractionated blood, hair, skin, and the like). In some cases, cells, fluids, or tissues derived from a subject are cultured, stored, or manipulated prior to evaluation and such a sample can be considered a diagnostic sample if the results are used to determine the presence, absence, state, or severity of a disease (e.g., sickness, diabetes, etc.) or condition (e.g., pregnancy) in a living organism.

In some instances, a diagnostic sample is a tissue sample (e.g., whole blood, fractionated blood, plasma, serum, saliva, and the like) or is obtained from a tissue sample (e.g., whole blood, fractionated blood, plasma, serum, saliva, skin, hair, and the like). An example of a diagnostic sample includes, but is not limited to cell and tissue cultures derived from a subject (and derivatives thereof, such as supernatants, lysates, and the like); tissue samples and body fluids; non-cellular samples (e.g., column eluants; acellular biomolecules such as proteins, lipids, carbohydrates, nucleic acids; synthesis reaction mixtures; nucleic acid amplification reaction mixtures; in vitro biochemical or enzymatic reactions or assay solutions; or products of other in vitro and in vivo reactions, etc.); etc.

The subject methods can be employed with samples from a variety of different types of subjects. In some embodiments, a sample is from a subject within the class mammalia, including e.g., the orders carnivore (e.g., dogs and cats), rodentia (e.g., mice, guinea pigs, and rats), lagomorpha (e.g. rabbits) and primates (e.g., humans, chimpanzees, and monkeys), and the like. In certain embodiments, the animals or hosts, i.e., subjects are humans.

Kits

Aspects of the invention further include kits, where kits include one or more assay devices, e.g., as described above. In some instances, the kits can include one or more assay components (e.g., labeled reagents, buffers, etc., such as described above). In some instances, the kits may further include a sample collection device, e.g., a lance or needle configured to prick skin to obtain a whole blood sample, a pipette, etc., as desired. The various assay components of the kits may be present in separate containers, or some or all of them may be pre-combined into a reagent mixture. For example, in some instances, one or more components of the kit, e.g., the device, are present in a sealed pouch, e.g., a sterile foil pouch or envelope.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

The following is offered by way of illustration, and not by way of limitation.

Experimental

I. Cell Surface CD4/Hb Assay

Figure 2A:
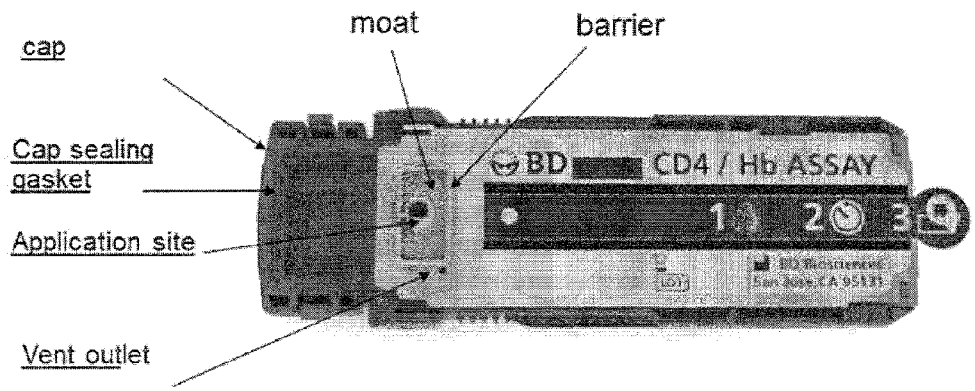
FIGS. 2A and 2B provide illustrations of assay devices according to embodiments of this invention.

FIG. 2A provides a depiction of a device according to an embodiment of the invention that is configured for performing a CD4 and hemoglobin (Hb) assay. The assay is carried out essentially as follows. A fingerstick amount (5-50 µL) of whole blood is loaded into a sample application site of a capillary device of this invention (shown in FIG. 2A) where it mixes with preloaded, dried preserved anti-human CD4 labeled with a suitable fluorescent label, such as allophycocyanine or phycoerythryn, and subsequently flows into a capillary channel. Once loaded, a cap is placed over the sample application site, sealing the sample application site and vent outlet of the capillary channel. Capillary flow proceeds along the channel, unimpeded by the cap sealing the capillary from the outside environment. Flow terminates at a hydrophobic junction. Labeled anti-CD4 binds to cells having surface CD4. Detection is carried out using an appropriate LED to illuminate the cartridge at one or more locations along the channel, and the fluorescence is measured by imaging through the top of the cartridge using a suitable imaging device, such as a low power microscope with a CCD-camera detector and an appropriate filter through the optically transmissive wall of the capillary channel. Fluorescence intensity on of cells in the channel may be quantified after image processing and analysis, as desired. For the hemoglobin assay, any convenient protocol may be carried out, including a reagent free protocol, e.g., as described in U.S. Pat. Nos. 8,483,789; 7,952,692; 7,319,894; 7,303,922; 7,271,912; 7,096,124; 7,075,628; 6,862,534; 6,831,733; and 5,773,301; and the like, the disclosure of which reagent free Hb assays described therein is herein incorporated by reference. Also present may be a region at the end of the microchannel for immobilized quality control (QC) reagent beads, which are coated with a known amount of CD4 that is bound by the labeled antibody reagent. A positive signal detected in this region confirms that reagent and sample flowed through the capillary channel to the hydrophobic junction, and therefore that the assay performed properly.

II. Anti-gp41 Assay

Figure 2B:
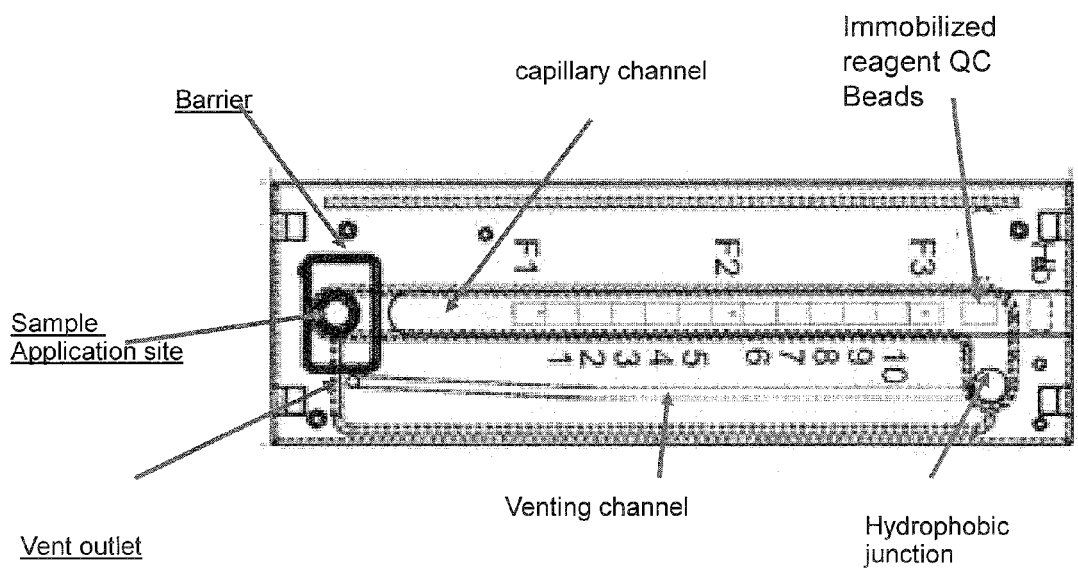

The assay is carried out essentially as follows. A fingerstick amount (5-50 µL) of whole blood is loaded into a sample application site of a capillary device of this invention (shown in FIG. 2B) where it mixes with preloaded, dried preserved anti-human antibody-allophycocyanine (APC), and subsequently flows into a capillary channel, which contains micro-particles coated with gp41 antigen (using HIV as an example) immobilized on the top surface of the channel. Once loaded, a cap is placed over the sample application site, sealing the sample application site and vent outlet of the capillary channel. Capillary flow proceeds along the channel, unimpeded by the cap sealing the capillary from the outside environment. Flow terminates at a hydrophobic junction. The anti-gp41 antibody present in the sample will bind to the micro-particle, resulting in the formation of bead-gp41/anti-gp 41 antibody/APC-anti-human antibody complexes. Detection is carried out using a red LED to illuminate the cartridge where the spot of beads is located, and the fluorescence is measured by imaging through the top of the cartridge using a low power microscope with a CCD-camera detector and an appropriate filter through the optically transmissive wall of the capillary channel. Fluorescence intensity on the micro-particles is quantified after image processing and analysis. For multiplexed assays, micro-particles coated with different disease-associated antigens are affixed in unique locations in the cartridge. Also shown is a region at the end of the microchannel for immobilized quality control (QC) reagent beads, which are coated with human antibody that is bound by the APC-anti-human antibody reagent. A positive signal detected in this region confirms that reagent and sample flowed through the capillary channel to the hydrophobic junction, and therefore that the assay performed properly.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A micro-fluidic device configured to perform an assay of a liquid sample, the device comprising:
   a sample application site in communication with a capillary channel;
   a vent outlet in communication with the capillary channel; and
   a capping element configured to seal both the vent outlet and the sample application site from an outside environment, wherein the capping element is configured to provide a sealed volume over the sample application site and the vent outlet separate from the outside environment and is configured to provide a sealed volume of a gas shared between the sample application site and the vent outlet.

2. The device according to claim 1, further comprising a venting channel between the vent outlet and the capillary channel.

3. The device according to claim 1, further comprising a liquid barrier surrounding the application site, wherein the liquid barrier is disposed between the application site and the vent outlet.

4. The device according to claim 3, wherein the liquid barrier comprises a raised edge surrounding the application site.

5. The device according to claim 3, wherein the liquid barrier comprises a depression surrounding the application site.

6. The device according to claim 1, wherein the capping element comprises a gasket.

7. The device according to claim 1, wherein the capillary channel is between 20 and 70 microns deep.

8. A method for performing an assay of a liquid sample, the method comprising:
   applying a liquid sample to a sample application site in fluid communication with a capillary channel wherein the liquid sample flows via a capillary action force through the capillary channel;
   providing venting for the capillary action force through a vent outlet; and
   sealing the liquid sample from the outside environment with a capping element, wherein the capping element provides a shared sealed volume around both the sample application site and the vent outlet.

9. The method according to claim 8, wherein the device further comprises a liquid barrier surrounding the application site and the liquid barrier is disposed between the application site and the vent outlet.

10. The method according to claim 9, wherein the liquid barrier comprises a raised edge surrounding the application site.

11. The method according to claim 9, wherein the liquid barrier comprises a depression surrounding the application site.

12. The method according to claim 8, wherein the capping element comprises a gasket.

13. The method according to claim 8, wherein the depth of the capillary channel is between 20 and 70 microns deep.

14. The method according to claim 8, wherein the method further comprises reading at least a portion of the capillary channel to obtain a result.

15. The method according to claim 14, wherein the method further comprises making a diagnosis based on the obtained result.

16. A system comprising:
(a) a reader; and
(b) a micro-fluidic device configured to perform an assay of a liquid sample and loaded into the reader, the device comprising:
a sample application site in communication with a capillary channel;
a vent outlet in communication with the capillary channel; and
a capping element configured to seal both the vent outlet and the sample application site from an outside environment, wherein the capping element is configured to provide a sealed volume over the sample application site and the vent outlet separate from the outside environment and is configured to provide a sealed volume of a gas shared between the sample application site and the vent outlet.

17. The system according to claim 16, wherein the reader comprises an illuminator and a detector.

18. The micro-fluidic device of claim 1, wherein the capping element is dimensioned to cover a surface area on a surface of the device that ranges from 10 to 1000 $mm^2$.

19. The micro-fluidic device of claim 18, wherein the capping contacts only a single surface of the device.

20. The micro-fluidic device of claim 1, wherein the capping element seals two openings.

21. The micro-fluidic device of claim 1, wherein the device further comprises a mixing chamber comprising a higher surface area component upon which a reagent is positioned.

22. The micro-fluidic device of claim 2, wherein the capillary channel is separated from the venting channel by a hydrophobic junction.

* * * * *